(12) United States Patent
Conti et al.

(10) Patent No.: US 9,901,559 B2
(45) Date of Patent: Feb. 27, 2018

(54) COMPOSITIONS COMPRISING AMINO ACIDS, WITH PRO-ANGIOGENIC ACTIVITY

(75) Inventors: Franco Conti, Milan (IT); Isabella Arborio Mella, legal representative, Milan (IT); Edoardo Carlo Marla Conti, legal representative, Milan (IT); Giovanni Federico Maria Conti, legal representative, Milan (IT); Francesco Saverio Dioguardi, Milan (IT)

(73) Assignee: Determinants of Metabolism Research Laboratory S.r.l., Castel San Giovanni (PC) (IT)

( * ) Notice: Subject to any disclaimer, the term of this patent is extended or adjusted under 35 U.S.C. 154(b) by 1027 days.

(21) Appl. No.: 12/996,426

(22) PCT Filed: Jun. 4, 2009

(86) PCT No.: PCT/IB2009/052373
§ 371 (c)(1),
(2), (4) Date: Mar. 11, 2011

(87) PCT Pub. No.: WO2009/147637
PCT Pub. Date: Dec. 10, 2009

(65) Prior Publication Data
US 2013/0085170 A1 Apr. 4, 2013

(30) Foreign Application Priority Data
Jun. 6, 2008 (IT) .............................. TO2008A0443

(51) Int. Cl.
*A61K 31/198* (2006.01)
*A61K 31/405* (2006.01)
*A61K 31/4172* (2006.01)
*A61K 45/06* (2006.01)

(52) U.S. Cl.
CPC .......... *A61K 31/198* (2013.01); *A61K 31/405* (2013.01); *A61K 31/4172* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,393,863 A | 7/1983 | Osterholm | |
| 6,218,420 B1 * | 4/2001 | Dioguardi | .................. 514/419 |
| 2004/0102504 A1 | 5/2004 | Dioguardi | |
| 2004/0192756 A1 | 9/2004 | Conti et al. | |
| 2007/0010437 A1 | 1/2007 | Dioguardi | |

FOREIGN PATENT DOCUMENTS

WO  WO 2005034932 A2 * 4/2005

OTHER PUBLICATIONS

Tonnesen et al. "Angiogenesis in Wound Healing", J.Invest.Derm. Symp.Proc., 2000, vol. 5, pp. 40-46.*
Brundin et al. "Effects of i.v. amino acids on human splanchnic and whole body oxygen consumption, blood flow, and blood temperatures", Am.J.Physiol.Endocrinol.Metab., 1994, vol. 266, pp. E396-E402.*
Turcotte et al. "Variation in mitochondrial function in hypoxia-sensitive and hypoxia-tolerant human glioma cells", Br.J.Cancer, 2002, vol. 86, pp. 619-624.*
Boudina et al. "Alteration of mitochondrial function in a model of chronic ischemia in vivo in rat heart", Am.J.Physiol.Heart Circ. Physiol., 2002, vol. 282, pp. H821-H831.*
Stefanovich, Anoxic Rat Model, Animal Models and Hypoxia, Proceedings of an International Symposium on Animal Models and Hypoxia, Held at Wiesbaden, Federal Republic of Germany, Nov. 19, 1979, pp. 111-124.*
Wegener, Comparative Aspects of Energy Metabolism in Nonmammalian Brains Under Normoxic and Hypoxic Conditions, Animal Models and Hypoxia, Proceedings of an International Symposium on Animal Models and Hypoxia, Held at Wiesbaden, Federal Republic of Germany, Nov. 19, 1979, pp. 87-109.*
Berlet et al., Chronic Normobaric Hypoxia and Subcellular Isoenzyme Patterns of Rat Brain Lactate Dehydrogenase, Animal Models and Hypoxia, Proceedings of an International Symposium on Animal Models and Hypoxia, Held at Wiesbaden, Federal Republic of Germany, Nov. 19, 1979, pp. 75-85.*
Brecht et al., "Protection from hypoxic injury in cultured hepatocytes by glycine, alanine, and serine", Amino Acids, 1994, vol. 6, pp. 25-35.*
International Search Report for PCT/IB2009/052373, dated Aug. 4, 2009.
Written Opinion for PCT/IB2009/052373, dated Aug. 4, 2009.
Killewich, L.A., et al, Journal of Vascular Surgery, vol. 45, No. 3, "Amino acids stimulate leg muscle protein synthesis in peripheral arterial disease", p. 554-561; Mar. 2007.

* cited by examiner

*Primary Examiner* — Jeffrey S Lundgren
*Assistant Examiner* — Stephanie K Springer
(74) *Attorney, Agent, or Firm* — Nixon & Vanderhye P.C.

(57) ABSTRACT

Composition comprising leucine, isoleucine, valine threonine and lysine for treating angiogenic disorders in elderly subjects.

3 Claims, 2 Drawing Sheets

40x Enlargement

Aged Mouse – non-treated group CA

Aged Mouse – treated group AA

100x Enlargement

Aged Mouse – non-treated group CA

Aged Mouse – treated group AA

COMPOSITIONS COMPRISING AMINO ACIDS, WITH PRO-ANGIOGENIC ACTIVITY

This application is the U.S. national phase of International Application No. PCT/IB2009/052373 filed 4 Jun. 2009 which designated the U.S. and claims priority to IT Patent Application No. TO2008A000443 filed 6 Jun. 2008, the entire contents of each of which are hereby incorporated by reference.

FIELD OF THE INVENTION

The present invention regards compositions with pro-angiogenic activity, suitable for treating tissue hypoxia in mammals. More specifically, the present invention concerns the use of compositions with pro-angiogenic activity comprising natural and non-natural amino acids for preventing, improving and treating tissue hypoxia in an elderly subject.

BACKGROUND ART

Hypoxia is a pathological condition characterised by low oxygenation of a tissue, organ or body region, and therefore the oxygen demand in the zone in question cannot be fully met. An increased metabolic demand in the zone in question, a partial or total reduction of blood supply due to loss or partial or total obstruction of blood vessels, a reduction of the amount of oxygen transported by the haemoglobin or the amount of oxygen in the haemoglobin itself are among the most common causes of hypoxia. In particular, the term tissue hypoxia is used to indicate a hypoxic phenomenon limited to a determined tissue.

The subjects most exposed to this pathological condition are the elderly, due to the fact that old age causes the natural reduction of the blood vessels and/or of the blood flow rate, particularly concerning the cardiac muscle and the brain. As a matter of fact, it has been proven that an elderly person reduces the number, flexibility and arborisation of vessels while the thickness of the wall of the vessel increases reducing the volume of the duct. This leads to poor blood perfusion and lower oxygen supply, which are principally the main causes of vascular and cerebrovascular problems observed in such subjects. Tissue hypoxia is also observable, in some forms, in non-elderly subjects, for example subjects affected by stenosis, i.e. the narrowing of the blood vessels, such to hinder normal blood flow.

An option for the treatment of subjects affected by tissue hypoxia consists in improving the tissue blood flow inducing the formation of new blood cells, or the "sprouting" of new blood vessels from pre-existing vessels, referred to as "angiogenesis" or "neoangiogenesis"; therapeutic interventions aimed at inducing the growth of the number of blood vessels are generally identified as "therapeutic angiogenesis". Currently, the treatments most commonly used in the field of therapeutic angiogenesis are based on the use of proteins or growth factors, such as for example FGF and VEGF. However, such treatments have some adverse effects difficult to bear for an elderly subject.

In some cases the elderly subjects were treated using the medical preparations deemed to be angiogenetic in an acute manner and for a short period of time. For example, in post operation conditions an intra-arterial, intravenous, intramuscular administration of such substances is deemed necessary: this kind of treatment may contribute to improving the general medical conditions of the patient, but it can simultaneously be a source of discomfort for the debilitated elderly subject and not intervene on the need for the revascularization of the damaged tissue.

It is clear that in the elderly subject, the reduced functionality of the cardiac muscle and of the cerebral activities, partially depending on the reduction of the amount of oxygen provided through blood supply, could benefit from an angiogenic process in the long run. Therefore, there arises the need for new compositions even administered over long periods of time, thus preferably for chronic use, such compositions being administered through non-invasive means, particularly oral means, and above all easily bearable by elderly subjects, and which are capable of activating an effective angiogenic process in the most deprived regions, such as heart and brain.

AIMS AND SUMMARY OF THE INVENTION

The present invention has the aim of providing new compositions for a prophylactic and therapeutic treatment, preferably but not exclusively intended for elderly subjects, of vascular and angiogenic disorders. Such object is attained through the technical solution outlined in the claims hereinafter.

In an embodiment, the composition described herein is particularly useful in the prophylactic and therapeutic treatment of angiogenic disorders determined by tissue hypoxia conditions, and comprises a mixture of amino acids in free form suitable for use over a long period of time.

The inventors found, in fact, that the combination of some free amino acids is surprisingly efficient at promoting angiogenesis or neoangiogenesis processes in mammals, i.e. increasing vascularisation and local oxygenation. In a preferred application, such mixture improves blood perfusion in subjects affected by tissue hypoxia, particularly in elderly subjects.

Therefore, the present invention regards compositions based on amino acids having pro-angiogenic activity in mammals having—as main active ingredients—the branched chain amino acid leucine in combination with at least one of, and preferably both, the branched chain amino acids isoleucine and valine. In a particular embodiment, the present invention concerns compositions comprising—as main active ingredients—the branched chain amino acids leucine, isoleucine and valine in combination with at least one of, and preferably both, threonine and lysine.

An advantage linked to the use of the compositions described herein lies in the high tolerability of the composition, which can be administered chronically. In a preferred embodiment, the administration may occur over a period of time sufficiently long to allow starting and continuing the angiogenic process, which is observed about 60 days after beginning the treatment.

A substantial advantage of the compositions subject of the invention is represented by the simple use of the same for the treated patients. The compositions are preferably produced, with or without excipients, according to known production, in formulations suitable for oral administration. In a preferred embodiment, the compositions described herein have a pH in aqueous solution comprised between 6.5 and 8.5, with or without excipients suitable for preparing tablets, capsules, powders, etcetera, through which a pharmacological performance suitable for oral administration is intended to be obtained. Also amino acids compositions produced, still according to per se known production techniques, for other types of administration shall be deemed comprised in the scope of the invention.

An advantage linked to the use of the composition described herein lies in the fact that the use of amino acids in free form allows producing such compositions at a comparatively extremely low cost with respect to proteins and growth factors synthesis, through per se known production processes and widely used in the field of preparing compositions based on free amino acids. The field of application of the invention may however also be extended to amino acids obtained through genetic engineering or any other artificial method.

BRIEF DESCRIPTION OF THE DRAWINGS

The invention shall now be described in a detailed manner, strictly for exemplifying and non-limiting purposes, with reference to the attached figures, wherein.

DETAILED DESCRIPTION OF PREFERRED EMBODIMENTS OF THE INVENTION

Figure 1:
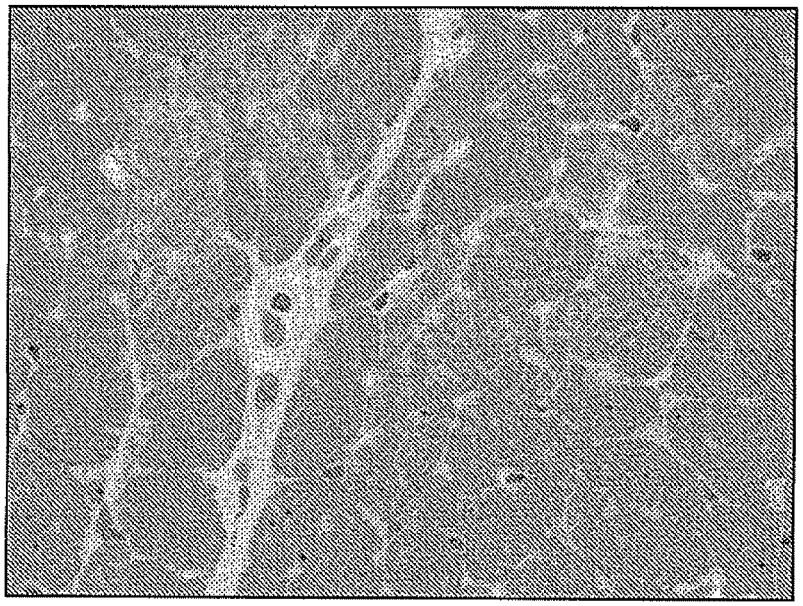
FIG. 1 represents a comparison of two images obtained by means of a microscope, with 40× enlargement, of respective semi-thin sections (about 0.5 μm thick) of heart samples, respectively of a treated and non-treated animal with a mixture of amino acids according to the invention.
Figure 1:
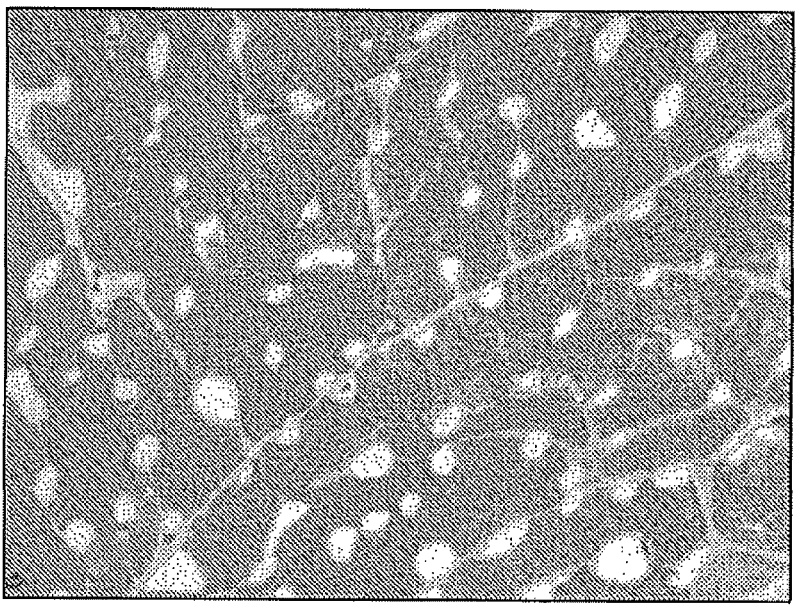

The compositions according to the invention comprise—as main active ingredients—the branched amino acid leucine in combination with at least one of, and preferably both, the branched amino acids isoleucine and valine. The preferred molar ratios of isoleucine and valine, with respect to one mole of leucine, are as follows:

isoleucine: from 0.2 to 0.7, preferably from 0.4 to 0.6;
valine: from 0.2 to 0.8, preferably from 0.4 to 0.7.

The inventors ascertained that the activity of the mixtures grew after adding at least one of, and preferably both, the amino acids threonine and lysine to the branched chain amino acids. More in detail, the preferred molar ratios of these amino acids, with respect to one mole of leucine, are as follows:

threonine: from 0.15 to 0.50, preferably from 0.2 to 0.45;
lysine: from 0.15 to 0.60, preferably from 0.3 to 0.55.

In particular, currently, the studies carried out by the inventors have demonstrated that the more efficient compositions are those in which, considering the sum of leucine, isoleucine and valine equal to 1, in the abovementioned stoichiometric ratio, then the sum of threonine and lysine is comprised between 0.10 and 0.50 (i.e. 1:0.10-0.50), still according to the molar weight, preferably between 0.25 and 0.45 (i.e. 1:0.25-0.45).

Studies carried out by the inventors have further shown that such compositions are more active in presence of further one or more essential amino acids selected from histidine, phenylalanine, methionine and tryptophan. Considering the sum of leucine, isoleucine, valine, threonine and lysine equanl to 1, then the overall amount of the further essential amino acids may vary between 0.02 to 0.25 (i.e. 1:0.02.-0.25), preferably from 0.05 to 0.15 (i.e. 1:0.05-0.15), still intended as the molar ratio.

The sum of the amount of threonine and lysine, still on the basis of the molecular weight, is preferably lower with respect to the sum of the single amounts of branched amino acids used, but greater with respect to the sum of the amount of the further essential amino acids used in the mixture. Furthermore, still preferably and n a molecular weight basis:

the amount of lysine is lower with respect to single amounts of the branched amino acids, but greater with respect to the single amounts of each of the further essential amino acids used in the mixtures (and hence even greater than the sum of the single amounts of such further essential amino acids, not considering threonine thereamong);

the amount of threonine is lower with respect to the single amounts of lysine and of the branched amino acids, but greater with respect to the single amounts of the further essential amino acids used in the mixtures, and much more preferably greater than the sum of the single amounts of the further essential amino acids.

In case methionine is used, the activity of the mixtures may be further enhanced by also providing for the insertion of the non-essential amino acid cystine (and/or cysteine) into the composition, in an amount of moles at least equivalent to that of methionine, and preferably comprised between 150 and 350% of methionine.

Alongside the abovementioned amino acids the compositions described herein may also comprise the non-essential amino acid tyrosine, whose ideal amount shall be comprised between 15 and 50%, preferably between 20 and 35%, of the amount of phenylalanine in moles.

Though the compositions may possibly comprise other amino acids with respect to the ones described above, the overall amount of said other amino acids shall not exceed 20% of the total of the active ingredients, and/or not exceed 10% per each single said other amino acid (still in molar weight). Furthermore, in particular, when preparing the compositions according to the invention, the amino acids serine, proline, glycine, alanine, glutamic acid and, above all, arginine, are preferably avoided, given that they can be counterproductive or even harmful in some cases.

The amino acids used in the experimentation that led to the identification of the indicated ratios are those of the levogyrous type, corresponding to those present in nature and which are thus to be considered the preferred active form. However, the inventors ascertained that also the racemic form may perform the same activity, though in a proportionally lower manner. Also the active derivatives of the indicated amino acids, in particular the salts thereof, shall obviously be deemed falling within the scope of the present invention.

Further specifications, in terms of amounts and ratios among the various amino acids provided for by the pro-angiogenic activity compositions are contained in the attached claims, which form an integral part of the technical teaching provided herein in relation to the invention.

Though expressed on the basis of molecular weight (i.e. in moles), the ratios indicated are applicable, in general terms, also in case of calculation according to the weight in grams of the various amino acids indicated (however bearing in mind that the amount of lysine, expressed in grams, may then be greater with respect to the single amounts of isoleucine and valine).

Following is a demonstration, by means of non-limiting examples, of the neo-angiogenic effects produced in mammals by the oral chronic administration of a composition of free amino acids obtained according to the invention. Such studies were performed in vivo on aged mice. Given that, in the case of elderly human beings, the organs most affected by vessel alterations with considerable consequences are the heart and brain, the study was mainly focused on the quantitative evaluation of the effects of the administration of the mixture on the vascularisation of the myocardium and of the cerebral cortex.

1. Materials and Methods

1.1 Animals and Treatments

The study was performed in compliance with the National Animal Protection Guidelines. Twenty aged C57BL/6 male mice (11 months old, mean weight 28.3±2 g at the beginning of the treatment) were used. The aged animals were divided into two groups: control group (CA, n=10) and group treated with the mixture of amino acids (AA, n=10). The animals were kept in rooms with controlled temperature and humidity, with artificial light/darkness cycle of 12/12 hours (7 a.m. to 7 p.m.). The animals of group CA were fed on a standard diet and ad libitum water, while those of group AA were supplemented for 90 days on a standard diet and 1.5 g/kg/day of the mixture of the amino acids dissolved in water. The weight of the animals, water consumption (group CA) and the consumption of the mixture of amino acids dissolved in water (group AA) were measured daily in each group. At the end of the treatment period the animals were deeply anesthetized and sacrificed through intraventricular perfusion using glutaraldeide 2.5% and paraformaldehyde 4% in PBS. The heart and the cerebral cortex were removed, post-fixed in 1% $OsO_4$ in PBS and included in araldite (Sigma Chemical Co, Milan, Italy) according to the producer's instructions.

Figure 2:
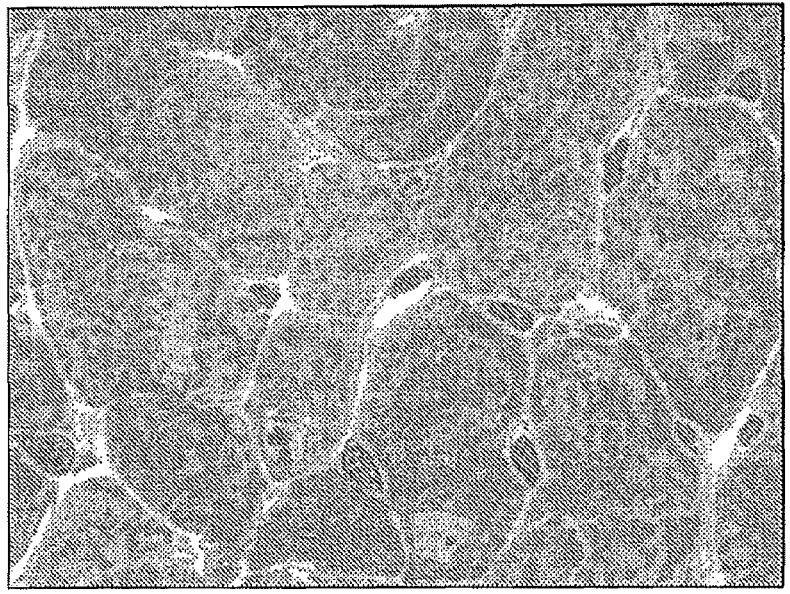
FIG. 2 represents a comparison of two images obtained from samples similar to the ones used for obtaining the images of FIG. 1, but with 100× enlargement.
Figure 2:
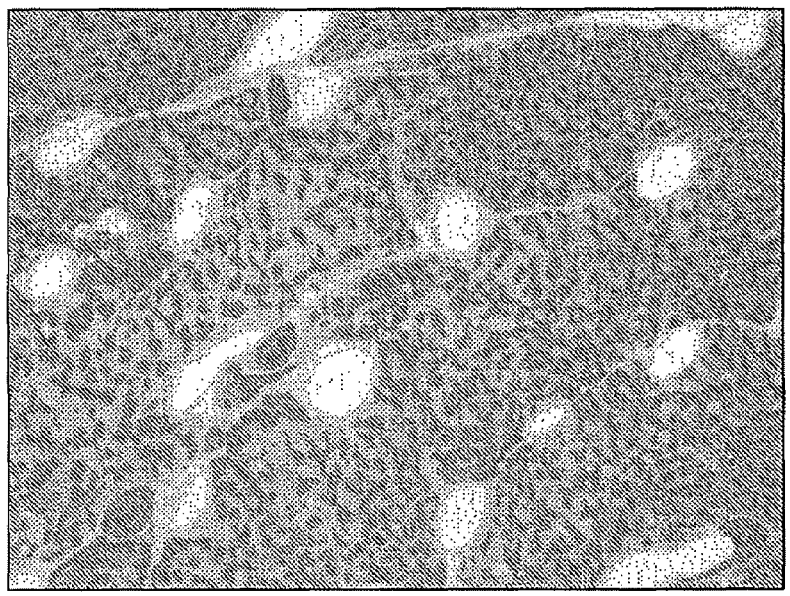

In order to evaluate the area and the density of the vessels in the heart and cerebral cortex samples, semi-thin sections—about 0.5 μm thick—stained with toluidine blue were made. Data was gathered on the optical microscope from fields randomly obtained at different tissue levels. The attached FIGS. 1 and 2 are images of respective fields obtained from the heart of a non-treated animal and of a treated animal, in various enlargements (40× and 100×, respectively).

Regarding the heart, 30 fields in the control animals (CA) and 44 fields in the treated animals (AA) respectively were examined.

Regarding the cerebral cortex, 27 fields both in the control animals (CA) and in the treated animals (AA) were examined.

1.2 Morphometrics

All the measurements were obtained using standard morphometric techniques, as described for example in the bibliographic references 1), 2) and 3). The following measurements were obtained from each of the examined fields:

Heart: total area of the field (ATot, $\mu m^2$), area of the myocardium (AMi, $\mu m^2$), area of the connective (ACo, $\mu m^2$), number of vessels (NVa), area of the vessel lumen (AVa, $\mu m^2$). This data was used to calculate the ACo/ATot, AVa/ATot ratios, as well as the number of vessels per unit area (NVa per 1000 $\mu m^2$);

Cerebral cortex: total area of the field (ATot, $\mu m^2$), number of vessels (NVa), area of the vessel lumen (AVa, $\mu m^2$). This data was used to calculate the AVa/ATot ratio and the number of vessels per unit area (NVa per 1000 $\mu m^2$).

1.3 Statistics

The morphometric data was expressed as the ±SD mean. The statistical significance of the difference between the means was evaluated through the Student t-test. A probability lower than 5% was deemed significant ($P<0.05$). Furthermore, a non-parametric test, the Mann-Whitney U test, was applied fixing the confidence interval at 95%.

2. Results

The mixture of amino acids used, obtained according to the principles indicated previously, is shown in the following table:

TABLE 1

| Amino acid | Molecular weight* | g/100 g | % on Tot. | % on group |
|---|---|---|---|---|
| L-Leucine | 131.17 | 31.2500 | 31.25% | 50.00% |
| L-Isoleucine | 131.17 | 15.6250 | 15.63% | 25.00% |
| L-Valine | 117.15 | 15.6250 | 15.63% | 25.00% |
| Branched group | | 62.5000 | 62.50% | 100.00% |
| L-Lysine | 146.19 | 16.2500 | 16.25% | 65.00% |
| L-Threonine | 119.12 | 8.7500 | 8.75% | 35.00% |
| Lysine + threonine group | | 25.0000 | 25.00% | 100.00% |
| L-Histidine | 155.16 | 3.7500 | 3.75% | 46.88% |
| L-Phenylalanine | 165.19 | 2.5000 | 2.50% | 31.25% |
| L-Methionine | 149.21 | 1.2500 | 1.25% | 15.63% |
| L-Tryptophan | 204.23 | 0.5000 | 0.50% | 6.25% |
| Further essentials group | | 8.0000 | 8.00% | 100.00% |
| L-Tyrosine | 181.19 | 0.7500 | 0.75% | |
| L-Cystine | 240.30 | 3.7500 | 3.75% | |
| Total composition | | 100.0000 | 100.00% | |

*from "Amino Acid, Nucleic Acids & Related Compounds - Specification/General Tests", 8th Edition, Kyowa Hakko Kogyo Co., Ltd.

In the following table, the amounts of composition in grams according to Table 1 are expressed according to the molecular weight, i.e. in moles.

TABLE 2

| Amino acid | Molecular weight | Mol | % on Tot. | % on group |
|---|---|---|---|---|
| L-Leucine | 131.17 | 0.23824 | 31.97% | 48.55% |
| L-Isoleucine | 131.17 | 0.11912 | 15.98% | 24.27% |
| L-Valine | 117.15 | 0.13338 | 17.90% | 27.18% |
| Branched group | | 0.49074 | 65.85% | 100.00% |
| L-Lysine | 146.19 | 0.11116 | 14.92% | 60.21% |
| L-Threonine | 119.12 | 0.07346 | 9.86% | 39.79% |
| Lysine + threonine group | | 0.18461 | 24.77% | 100.00% |
| L-Histidine | 155.16 | 0.02417 | 3.24% | 48.21% |
| L-Phenylalanine | 165.19 | 0.01513 | 2.03% | 30.19% |
| L-Methionine | 149.21 | 0.00838 | 1.12% | 16.71% |
| L-Tryptophan | 204.23 | 0.00245 | 0.33% | 4.88% |
| Further essentials group | | 0.05013 | 6.73% | 100.00% |
| L-Tyrosine | 181.19 | 0.00414 | 0.56% | |
| L-Cystine | 240.30 | 0.01561 | 2.09% | |
| Total composition | | 0.74522 | 100.00% | |

As observable from Table 1, the weight ratios between leucine, isoleucine and valine are preferably equivalent to 2:1:1. Table 1 and Table 2 also show that the single amounts (weight in grams or moles) of histidine, phenylalanine, methionine and tryptophan are preferably decreasing (i.e. the amount of histidine is greater than phenylalanine, which is greater than methionine, which is greater than tryptophan) and the amount (weight in grams or moles) of cystine (and/or cysteine) is preferably greater than tyrosine. After the treatment, the mean weight, as well as the mean daily consumption of food, water or aqueous solution and amino acids in the two groups of animals (control and treated) are summarised in Table 3. There were no significant variations in the body weight and in the consumption of liquids and food in the animals that received the supplement with the mixture of amino acids (treated animals identified with AA with respect to non-treated animals identified with CA).

TABLE 3

|  | CA (n = 10) | AA (n = 10) |
| --- | --- | --- |
| Body mass (g) | 28 ± 2.1 | 29.14 ± 3.43 |
| Food consumption (g/day) | 4.71 ± 0.63 | 4.10 ± 0.54 |
| Water consumption (ml/day) | 6.36 ± 1.54 | — |
| Water consumption + mixture of amino acids (ml/day) | — | 5.72 ± 0.41 |

However, a significant variation of the morphometric parameters of the cardiac tissue and of the cerebral cortex with respect to the control animals of the same age was observed in animals treated using a mixture of amino acids.

The results regarding the heart are shown in Table 4, where data regarding the comparison between the morphometric measures obtained from semithin sections of the heart of aged control (CA) and treated (AA) animals was provided. Table 5 shows the results regarding comparison between the morphometric measurements obtained from semi-thin sections of the cerebral cortex of aged control (CA) and treated (AA) animals.

TABLE 4

| Heart- | | | |
| --- | --- | --- | --- |
|  | CA (n = 30) | AA (n = 44) | Δ % |
| Total area μm² (ATot) | 720,000.00 | 1,007,343.75 | — |
| Total number of vessels (NVa) | 1648 | 3.070 | — |
| Total area myocardium μm² (AMi) | 686,562.50 | 984,062.50 | — |
| Total area of connective μm² (ACo) | 33,437.50 | 23,281.25 | — |
| Total area of vessels (lumen) μm² (AVa) | 8,087.50 | 61,843.75 | — |
| ACo/ATot | 0.05 ± 0.01 | 0.03 ± 0.01** | −40 |
| NVa per 1000 μm² | 2.29 ± 0.54 | 3.05 ± 0.53** | +33 |
| AVa/ATot | 0.011 ± 0.003 | 0.06 ± 0.015** | +465 |

**= $p < 0.01$

After treatment using the mixture of amino acids in elderly subjects of group AA there is a reduction of the ACo/ATot ratio by 40%, indicating a reduction of fibrosis. Above all, at vessel level there is a 33% increase of density per unit area (NVa per 1000 μm²) associated to a significant approximate 465% increase of the ratio between the area of the vessel lumen and the total examined area (AVa/ATot).

The images in FIGS. 1 and 2 allow an immediate visual observation of the considerable capacity of the mixture to induce the vascularisation of the examined tissues: alongside the increase of the number of capillaries, the images also show a considerable increase of the lumen thereof in aged treated animals, with respect to non-treated animals.

TABLE 5

| Cerebral cortex- | | | |
| --- | --- | --- | --- |
|  | CA (n = 27) | AA (n = 27) | Δ % |
| Total area μm² (ATot) | 648,437.50 | 649,218.75 | — |
| Total number of vessels (NVa) | 166 | 292 | — |
| Total area of vessels (lumen) μm² (Ava) | 2,381.25 | 5,562.50 | — |
| NVa per 1000 μm² | 0.26 ± 0.14 | 0.45 ± 0.13** | +72 |
| AVa/ATot | 0.004 ± 0.002 | 0.01 ± 0.002** | +125 |

**= $p < 0.01$

There is an approximate 70% increase of the density of the vessels per unit area (NVa per 1000 μm²) associated to an approximate 125% increase of the ratio between the area of the vessel lumen and the total area examined (AVa/ATot).

Therefore, the prolonged treatment of elderly subjects using the described mixture allowed to increase the vascularisation, hence improving blood profusion and likewise the functionality of the heart and of the cerebral cortex. This shows that the mixtures obtained according to the invention have a significant pro-angiogenic activity in aged mammals.

In conclusion, the composition of free amino acids proposed in the present invention find application in the field of therapeutic angiogenesis, as an alternative to the therapeutic options already in use. The compositions of the present invention are suitable for treating vascular and angiogenic alterations/disorders, particularly those linked to tissue hypoxia.

Though the activity of the mixture was tested with particular reference to the heart and brain, the principles of the invention shall be deemed also applicable to other organs, with therapeutic or preventive angiogenic purposes.

The compositions according to the invention are provided for chronic or prolonged use, i.e. with administration preferably extended over at least 60 days, in such a manner to stimulate the formation of new vessels along all the steps of the angiogenic process and intended particularly for the elderly, i.e. the subjects most affected by the reduction of the number of blood vessels. The compositions according to the invention find specific use in elderly subjects, but they can be beneficial also in non-elderly subjects affected by vascularisation disorders, for example in presence of stenosis or other angiogenic disorders.

The invention claimed is:

1. A method for treating an angiogenic disorder in a mammal, comprising orally administering thereto a therapeutically effective amount of a pharmaceutical composition comprising
   31.25% w/w leucine,
   15.63% w/w isoleucine,
   15.63% w/w valine,
   16.25% w/w lysine,
   8.75% w/w threonine,
   3.75% w/w histidine,
   2.50% w/w phenylalanine,
   1.25% w/w methionine,
   0.50% w/w tryptophan,
   0.75% w/w tyrosine, and
   3.75% w/w cystine,
   wherein the angiogenic disorder is one of hypoxia and stenosis, and
   wherein the pharmaceutical composition has a pro-angiogenic activity that results in the method having a pro-angiogenic activity in the mammal.

2. The method according to claim 1, wherein the angiogenic disorder affects one of the cardiac muscle and the brain.

3. The method according to claim 1, wherein the composition is administered chronically over at least 60 days.

* * * * *